(12) United States Patent
Okumura et al.

(10) Patent No.: US 10,472,338 B2
(45) Date of Patent: Nov. 12, 2019

(54) METHOD FOR PRODUCING [$^{18}$F]FLUTEMETAMOL

(71) Applicants: GE Healthcare Limited, Buckinghamshire (GB); Nihon Medi-Physics Co., Ltd., Tokyo (JP)

(72) Inventors: Yuki Okumura, Tokyo (JP); Gota Tonoya, Tokyo (JP); Tomoyuki Matsunami, Tokyo (JP)

(73) Assignees: GE HEALTHCARE LIMITED, Buckinghamshire (GB); NIHON MEDI-PHYSICS CO., LTD., Tokyo (JP)

( * ) Notice: Subject to any disclaimer, the term of this patent is extended or adjusted under 35 U.S.C. 154(b) by 0 days.

(21) Appl. No.: 15/764,309

(22) PCT Filed: Oct. 17, 2016

(86) PCT No.: PCT/EP2016/074840
§ 371 (c)(1),
(2) Date: Mar. 28, 2018

(87) PCT Pub. No.: WO2017/071980
PCT Pub. Date: May 4, 2017

(65) Prior Publication Data
US 2019/0055207 A1    Feb. 21, 2019

(30) Foreign Application Priority Data
Oct. 28, 2015 (JP) .................. 2015-211413

(51) Int. Cl.
*C07D 277/66* (2006.01)

(52) U.S. Cl.
CPC ............ *C07D 277/66* (2013.01); *Y02P 20/55* (2015.11)

(58) Field of Classification Search
CPC .................................................. C07D 277/66
See application file for complete search history.

(56) References Cited

U.S. PATENT DOCUMENTS

| 8,323,616 B2* | 12/2012 | Brady | A61K 51/0453 |
| | | | 424/1.65 |
| 8,969,580 B2* | 3/2015 | Horn | A61K 51/0402 |
| | | | 548/178 |
| 9,126,961 B2* | 9/2015 | Storey | C07D 277/66 |
| 9,346,771 B2* | 5/2016 | Horn | A61K 51/0402 |

FOREIGN PATENT DOCUMENTS

| WO | 2004083195 A1 | 9/2004 |
| WO | 2006133732 A1 | 12/2006 |
| WO | 2007020400 A1 | 2/2007 |
| WO | 2011044406 A2 | 4/2011 |
| WO | 2017071980 A1 | 5/2017 |

OTHER PUBLICATIONS

Liu et al. Food Chemistry 204 (2016) 56-61. (Year: 2016).*
Burdge et al. British Journal of Nutrition (2000), 84, 781-787. (Year: 2000).*
GE Handbook: "Strategies for Protein Purification Handbook". (Year: 2010).*
International Search Report and the Written Opinion of the International Searching Authority, or the Declaration from International Appl. No. PCT/EP2016/074840, dated Nov. 28, 2016.

* cited by examiner

*Primary Examiner* — Golam M Shameem
(74) *Attorney, Agent, or Firm* — Arent Fox LLP

(57) ABSTRACT

Provided is a method for producing flutemetamol including the steps of: reacting a precursor compound represented by a predetermined general formula with a radioactive fluoride to obtain a $^{18}$F labeling compound represented by a predetermined general formula; allowing a strong base to act on the reaction mixture of the above step containing the precursor compound and the $^{18}$F labeling compound; after the above step, purifying the $^{18}$F labeling compound using a reverse phase solid phase extraction cartridge; and removing a protective group to obtain [$^{18}$F]flutemetamol.

20 Claims, No Drawings

METHOD FOR PRODUCING [$^{18}$F]FLUTEMETAMOL

CROSS-REFERENCE TO RELATED APPLICATIONS

The application is a filing under 35 U.S.C. 371 of international application number PCT/EP2016/074840, filed Oct. 17, 2016, which claims priority to application number 2015-211413 filed in Japan on Oct. 28, 2015, the entire disclosures of each of which are hereby incorporated by reference.

FIELD OF THE INVENTION

The present invention relates to a method for producing flutemetamol.

BACKGROUND OF THE INVENTION

Flutemetamol ($^{18}$F) Injection is an agent used for visualizing β-amyloid beta plaques in the brain by positron emission tomography, and is useful in diagnosis of Alzheimer type dementia.

As a method for producing [$^{18}$F]flutemetamol, for example, using a radiopharmaceutical synthesizer "FAST-lab", a method of reacting AH111907 (6-ethoxymethoxy-2-(4'-(N-formyl-N-methyl)amino-3'-nitro)phenylbenzothiazole) with a radioactive fluoride to replace the nitro group of AH111907 by $^{18}$F, then converting AH111907 residue into a less fat-soluble substance by a strong base, removing protective groups of the hydroxy group and amino group of the $^{18}$F substitution product of AH111907 (6-ethoxymethoxy-2-(4'-(N-formyl-N-methyl)amino-3'-[$^{18}$F]fluoro)phenylbenzothiazole), then performing purification using a solid phase extraction cartridge is known (WO2011/044406).

However, the yield of [$^{18}$F]flutemetamol is low in the method described in WO2011/044406, thus, delivery to a wide range by mass production has been difficult. Therefore, in order to supply [$^{18}$F]flutemetamol formulation to more patients, it has been required to improve productivity.

SUMMARY OF THE INVENTION

The present invention has been made in consideration of the above situation, and an object of the present invention is to improve productivity of [$^{18}$F]flutemetamol.

According to an aspect of the present invention, there is provided a method for producing flutemetamol including the steps of:

(a) reacting a compound represented by the following general formula (1) with a radioactive fluoride to obtain a compound represented by the following general formula (2);

(b) allowing a strong base to act on the reaction mixture of the step (a) containing the compound represented by the following general formula (1) and the compound represented by the following general formula (2);

(c) after the step (b), purifying the compound represented by the following general formula (2) using a reverse phase solid phase extraction cartridge; and (d) removing a protective group to obtain [$^{18}$F]flutemetamol.

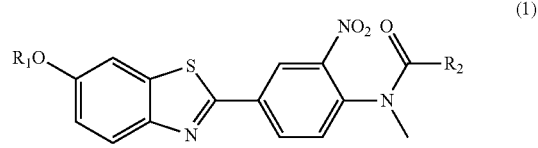

wherein $R_1$ is a protective group of hydroxy, and $C(O)R_2$ represents a protective group of amino.

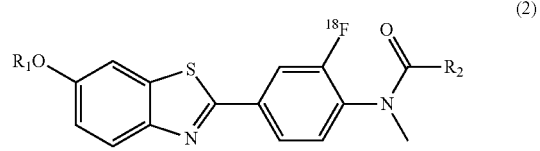

wherein $R_1$ and $R_2$ have the same meaning as in the compound represented by the general formula (1).

According to the present invention, productivity of [$^{18}$F]flutemetamol can be improved.

DETAILED DESCRIPTION

The term "alkyl" herein used alone or as a part of the other group denotes a saturated or branched saturated hydrocarbon group such as methyl, ethyl, propyl, isopropyl, butyl, isobutyl, tert-butyl, n-pentyl or n-hexyl.

Further, the term "haloalkyl" herein used alone or as a part of the other group denotes one in which one or more hydrogen of alkyl is replaced by fluorine, chlorine, bromine, or iodine.

Moreover, the term "alkoxy" herein used alone or as a part of the other group denotes a saturated or branched saturated hydrocarbon group such as methoxy, ethoxy, propoxy, isopropoxy, butoxy, isobutoxy, tert-butoxy, n-pentoxy, or n-hexyloxy.

Further, the term "aryl" herein used alone or as a part of the other group denotes a monocyclic or condensed ring aromatic hydrocarbon such as phenyl or naphthyl.

(a) $^{18}$F Labeling Step

In the $^{18}$F labeling step, the compound represented by the general formula (1) (hereinafter, also referred to as "labeling precursor compound") is reacted with a radioactive fluoride to obtain a compound represented by the following general formula (2) (hereinafter, also referred to as "$^{18}$F labeling intermediate compound").

As the protective group of hydroxy of $R_1$, those described in Greene's Protective Groups in Organic Synthesis (published by Wiley-Interscience, 4th edition, issued on Oct. 30, 2006) can be used. The group represented by $OR_1$ is preferably an alkoxymethoxy group having 1 to 6 carbon atoms, and examples include an ethoxymethoxy group and a methoxymethoxy group.

$R_2$ is selected from hydrogen, alkyls having 1 to 10 carbon atoms, haloalkyls having 1 to 10 carbon atoms, aryls having 6 to 14 carbon atoms, arylalkyls having 6 to 14 carbon atoms, and —$(CH_2CH_2O)_p$—$CH_3$ wherein p is an integer of 1 to 10. $R_2$ is preferably hydrogen or an alkyl having 1 to 10 carbon atoms, more preferably hydrogen or methyl, and further preferably hydrogen.

The labeling precursor compound can be synthesized, for example, using a method described in WO2007/020400. A preferred example of the labeling precursor compound is 6-ethoxymethoxy-2-(4'-(N-formyl-N-methyl)amino-3'-nitro)phenylbenzothiazole (AH111907), and an example of the synthesis method thereof is described in Example 1 of WO2007/020400.

The radioactive fluoride can be obtained by adding a cationic counter ion to an aqueous solution containing a [$^{18}$F]fluoride ion obtained from [$^{18}$O]water by $^{18}$O (p,n)$^{18}$F nuclear reaction to remove water. The cationic counter ion is preferably one having sufficient solubility in an anhydrous reaction solvent, so that the solubility of the [$^{18}$F]fluoride ion can be maintained. Examples include tetraalkyl ammonium and alkali metal ions (sodium ion, potassium ion, cesium ion, rubidium ion) forming a complex with a phase transfer catalyst (for example, 4,7,13,16,21,24-hexaoxa-1,10-diazabicyclo[8.8.8]hexacosane (trade name: Kryptofix 2.2.2)), and tetrabutyl ammonium is preferred. [$^{18}$F]Tetrabutyl ammonium fluoride can be prepared, for example, by passing the [$^{18}$F]fluoride ion-containing [$^{18}$O]water obtained by $^{18}$O (p,n)$^{18}$F nuclear reaction through an anion-exchange resin to adsorb the [$^{18}$F]fluoride ion to the anion-exchange resin, eluting it with an aqueous solution of tetrabutylammonium hydrogen carbonate, and forming an azeotropic mixture with acetonitrile.

The $^{18}$F labeling step may be carried out in an appropriate solvent. As the solvent, as acetonitrile, dimethylformamide, dimethyl sulfoxide, dimethylacetamide, tetrahydrofuran, dioxane, 1,2-dimethoxyethane, sulfolane, N-methylpyrrolidone, an imidazolium derivative such as 1-butyl-3-methylimidazolium hexafluorophosphate, a pyridinium derivative such as 1-butyl-4-methylpyridinium hexafluoroborate, a phosphonium compound, or an ionic liquid such as a tetraalkylammonium compound can be used, and dimethyl sulfoxide is preferred.

The $^{18}$F labeling step can be, for example, carried out at the range of 15 to 180° C., preferably 80 to 150° C., and more preferably 120 to 140° C., and carried out further preferably at around 130° C.

(b) Precursor Decomposition Step

In the precursor decomposition step, a strong base is allowed to act on the reaction mixture in the $^{18}$F labeling step containing the labeling precursor compound and the $^{18}$F labeling intermediate compound. Thereby, the labeling precursor compound residue contained in the reaction mixture in the $^{18}$F labeling step is converted into a highly polar compound. As the highly polar compound, those shown in FIG. 1 of WO2011/044406 can be considered. In the precursor decomposition step, the $^{18}$F labeling intermediate compound remains without reacting with a strong base.

The strong base includes alkali metal alkoxides, alkali metal hydroxides and the like, and sodium methoxide, sodium ethoxide, sodium hydroxide, potassium hydroxide, sodium hydride or methylmercaptan sodium is preferably used. The strong base is more preferably sodium methoxide or sodium ethoxide, and further preferably sodium methoxide.

The precursor decomposition step is preferably carried out in the presence of a solvent. The solvent includes alkyl alcohols, and methanol is preferred.

The precursor decomposition step can be, for example, carried out at the range of 15 to 180° C., preferably 80 to 150° C., and more preferably 120 to 140° C., and carried out further preferably at around 130° C.

(c) First Purification Step

In the first purification step, after the precursor decomposition step, the $^{18}$F labeling intermediate compound is purified using a reverse phase solid phase extraction cartridge. Thereby, the $^{18}$F labeling intermediate compound, and the highly polar compound obtained in the precursor decomposition step are separated.

As the reverse phase solid phase extraction cartridge, one using a filler in which a silyl group is modified with alkyl having preferably 8 or more carbon atoms and more preferably 18 or more carbon atoms is used, and a solid phase extraction cartridge packed with triacontyl silylated silica gel in which a silyl group is modified with 30 carbon atoms is further preferably used. Such reverse phase solid phase extraction cartridge is commercially available, for example, from Macherey-Nagel. The reverse phase solid phase extraction cartridge is preferably conditioned with acetonitrile and water before use.

Purification of the $^{18}$F labeling intermediate compound using a reverse phase solid phase extraction cartridge is not particularly limited as long as it is carried out using a technique of normal solid phase extraction method. An example will be explained below.

First, the $^{18}$F labeling intermediate compound through the precursor decomposition step is held in a reverse phase solid phase extraction cartridge [(c-1) holding step]. Preferably, after the precursor decomposition step, the reaction mixture containing the $^{18}$F labeling intermediate compound and the highly polar compound described above is diluted by adding water, and loaded on a reverse phase solid phase extraction cartridge.

Subsequently, the reverse phase solid phase extraction cartridge is washed with a mixture liquid of water and one or more organic solvents selected from a group consisting of acetonitrile, tetrahydrofuran and alkyl alcohols having 1 to 3 carbon atoms [(c-2) washing step]. The solvent used for washing is preferably a mixture liquid of water and acetonitrile, and as the mixing ratio thereof, for example, the content of acetonitrile can be 35 to 45% by volume, and preferably 39.5 to 40.5% by volume of the entire mixture liquid. The temperature of the reverse phase solid phase extraction cartridge is preferably in the range of 19 to 34° C. and more preferably in the range of 20 to 30° C. This washing step may be repeated for a plurality of times. Thereby, the highly polar compound described above can be eluted from the reverse phase solid phase extraction cartridge, while holding the $^{18}$F labeling intermediate compound in a reverse phase solid phase extraction cartridge.

Thereafter, the $^{18}$F labeling intermediate compound is eluted with an alkyl alcohol having 1 to 3 carbon atoms from the reverse phase solid phase extraction cartridge [(c-3) elution step]. The alkyl alcohol having 1 to 3 carbon atoms includes methanol, ethanol, 1-propanol, and 2-propanol, and ethanol is more preferable from the viewpoint of safety. At this time, nitrogen gas may be flown from the inlet port of the reverse phase solid phase extraction cartridge or sucked from the discharge port. The obtained eluate can be used in the next step as it is or after concentrating the solvent under heating or reduced pressure.

(d) Deprotection Step

In the deprotection step, protective groups of the hydroxy group and amino group are each removed to obtain [$^{18}$F] flutemetamol.

The deprotection step may be carried out in accordance with the description of Greene's Protective Groups in Organic Synthesis (published by Wiley-Interscience, 4th edition, issued on Oct. 30, 2006), and it is preferred to carry out acid hydrolysis using an organic acid or inorganic acid. As the acid, an inorganic acid such as sulfuric acid, hydrochloric acid, phosphoric acid or hydrobromic acid is preferably used, and hydrochloric acid is more preferably used.

The deprotection step can be carried out in the presence of water, an organic solvent such as an alkyl alcohol having 1 to 4 carbon atoms or acetonitrile or a mixture liquid thereof, and it is preferred to add an acid to an ethanol eluate obtained by the elution step of the first purification step and then carry out the deprotection step.

The deprotection step is preferably carried out at 100° C. or more.

(e) Second Purification Step

In the second purification step, after the deprotection step, the [$^{18}$F]flutemetamol is purified using a reverse phase solid phase extraction cartridge.

As the type of the reverse phase solid phase extraction cartridge used in the second purification step, one that can be used in the first purification step can be used, and a solid phase extraction cartridge packed with triacontyl silylated silica gel in which a silyl group is modified with 30 carbon atoms is preferably used.

Purification of the [$^{18}$F]flutemetamol using a reverse phase solid phase extraction cartridge is not particularly limited as long as it is carried out using a technique of normal solid phase extraction method. An example will be explained below.

First, the [$^{18}$F]flutemetamol through the deprotection step is held in a reverse phase solid phase extraction cartridge [(e-1) holding step]. Preferably, after the deprotection step, the crude product of [$^{18}$F]flutemetamol is diluted by adding water, so that the content of the organic solvent taken from the previous step (for example, ethanol taken from the first purification step) is 50% by volume or less, and loaded on a reverse phase solid phase extraction cartridge.

Subsequently, the reverse phase solid phase extraction cartridge is washed with water or a mixture liquid of water and one or more organic solvents selected from a group consisting of acetonitrile, tetrahydrofuran and alkyl alcohols having 1 to 3 carbon atoms [(e-2) washing step]. The solvent used for washing is preferably a mixture liquid of water and acetonitrile, and as the mixing ratio thereof, for example, the content of acetonitrile can be 35 to 45% by volume, and preferably 39.5 to 40.5% by volume of the entire mixture liquid. The temperature of the reverse phase solid phase extraction cartridge is preferably in the range of 19 to 34° C. and more preferably in the range of 20 to 30° C. This washing step may be repeated for a plurality of times, and at this time, the reverse phase solid phase extraction cartridge is preferably washed with water. Thereby, unnecessary solvent and the deprotecting reagent can be removed, while holding the [$^{18}$F]flutemetamol in the reverse phase solid phase extraction cartridge.

Thereafter, the [$^{18}$F]flutemetamol is eluted with ethanol from the reverse phase solid phase extraction cartridge [(e-3) elution step]. Thereafter, water may be further passed through and combined with the eluate. Furthermore, nitrogen gas may be flown from the inlet port of the reverse phase solid phase extraction cartridge or sucked from the discharge port.

(f) Third Purification Step

In the third purification step, after the second purification step, the [$^{18}$F]flutemetamol is purified using a hydrophilic interaction (HILIC) solid phase extraction cartridge.

As the HILIC solid phase extraction cartridge, for example, one packed with silica gel, or silica gel in which a highly polar functional group such as amino, amide, cyano, diol, a polysuccinimide derivative, zwitterion or cyclodextrin is introduced can be used. Here, a silica gel-based amino solid phase is preferable, and one packed with aminopropylated silica gel is more preferable. Thereby, impurities can be captured with the HILIC solid phase extraction cartridge, while allowing the [$^{18}$F]flutemetamol to pass through. Such HILIC solid phase extraction cartridge is commercially available, for example, from Waters, Agilent Technologies, and the like. The HILIC solid phase extraction cartridge is preferably conditioned by passing acetonitrile or ethanol before use, followed by flowing nitrogen to be dried.

Subsequently, the eluate obtained in the second purification step is directly allowed to pass through the HILIC solid phase extraction cartridge. Thereafter, water may be passed through, and the eluate may be combined. Furthermore, nitrogen gas may be flown from the inlet port of the HILIC solid phase extraction cartridge or sucked from the discharge port.

The obtained eluate may contain a pharmaceutically acceptable carrier, diluent, emulsion, excipient, extender, dispersant, buffer, preservative, solubilizer, antiseptic, colorant, stabilizer, and the like, so as to have a form suitable for administration of [$^{18}$F]flutemetamol to a living body, preferably a form of injection. The obtained [$^{18}$F]flutemetamol-containing solution is desirably filtered with a membrane filter.

The formulation example of [$^{18}$F]flutemetamol is, for example, disclosed in WO2009/027452.

According to the method of the present invention described above, the first purification step conventionally carried out after the deprotection step is carried out after the $^{18}$F labeling step and before the deprotection step. When the first purification step is carried out after the deprotection step, many impurities containing the highly polar compound derived from the labeling precursor compound are present, thus the loss of [$^{18}$F]flutemetamol increases with the removal of impurities. On the other hand, the first purification step is carried out before the deprotection step, whereby the highly polar compound derived from the labeling precursor compound can be removed before the deprotection step. Thereby, the $^{18}$F labeling intermediate compound can be purified while preventing the loss of the $^{18}$F labeling intermediate compound, that is an intermediate compound of the [$^{18}$F]flutemetamol, thus [$^{18}$F]flutemetamol can be obtained in a higher yield than a conventional one and with a quality equivalent to a conventional one. Therefore, according to the present invention, productivity of [$^{18}$F]flutemetamol can be improved.

EXAMPLES

Hereinafter, the present invention will be further preferably described in detail with reference to the examples, but the present invention is not limited to the content of the examples. Here, as the reagent and column member used in the examples, a component of a radiopharmaceutical synthesizer FASTlab (for synthesis of flutemetamol) manufactured by GE Healthcare or a component equivalent to the same was used.

Examples 1 to 3

(a) $^{18}$F Labeling Step

[$^{18}$F]Fluoride ion-containing [$^{18}$O]water obtained by proton irradiation of [$^{18}$O]water using a cyclotron was passed through an anion-exchange column, and the [$^{18}$F]fluoride ion was adsorbed and collected. Subsequently, the column was washed with water (3 mL), then eluted using a 0.15 mol/L aqueous solution of tetrabutylammonium hydrogen carbonate (0.35 mL) and acetonitrile (1 mL), and the obtained eluate was evaporated. Thereto was added a dimethyl sulfoxide solution (1 mL) of 6-ethoxymethoxy-2-(4'-(N-formyl-N-methyl)amino-3'-nitro)phenylbenzothiazole (AH111907) (75 μmol), and the mixture was heated at 130° C. for 15 minutes, then cooled.

(b) Precursor Decomposition Step

A methanol solution (11% (w/w), 1 mL) of sodium methoxide was added to the reaction liquid after cooling in the step (a), and the mixture was heated at 130° C. for 5 minutes, and cooled.

(c) First Purification Step

Water (2 mL) was added to the reaction liquid after cooling in the step (b), and the mixture was passed through a triacontyl silylated silica gel (C30) column to hold the $^{18}$F labeling intermediate compound. Furthermore, washing was carried out by passing a 40% (v/v) aqueous acetonitrile solution (6 mL) through the C30 column via a reaction vessel, then washing was again carried out by directly passing a 40% (v/v) aqueous acetonitrile solution (6 mL) through the C30 column. Ethanol (2 mL) was passed through this C30 column to collect an eluate.

(d) Deprotection Step

A 4 mol/L hydrochloric acid (2.0 mL) was added to the eluate collected in the step (c), and the mixture was heated at 125° C. for 5 minutes to obtain an unpurified [$^{18}$F]flutemetamol solution.

(e) Second Purification Step

The unpurified [$^{18}$F]flutemetamol solution obtained in the step (d) was cooled, then water (10 mL) was added thereto, and the mixture was passed through an unused C30 column different from the one used in the step (b) to hold the [$^{18}$F]flutemetamol in the C30 column. Washing was carried out by passing a 40% (v/v) aqueous acetonitrile solution (6 mL) through the C30 column, then washing was carried out by passing water (6 mL). The [$^{18}$F]flutemetamol was eluted with ethanol (3.5 mL) from the C30 column.

(f) Third Purification Step

The eluate in the step (e) was passed through a column (NH$_2$ column) packed with aminopropylated silica gel. Washing was carried out by passing water (9.3 mL) through the C30 column used in the step (e) and the NH$_2$ column, in this order, and each eluate was collected in a vessel to which a 18.8 mmol/L phosphoric acid buffer (37.2 mL) containing 0.7% (w/v) polysorbate 80 and 1.2% (w/v) sodium chloride were added.

Comparative Examples 1 and 2

The steps (a) and (b) of Examples 1 to 3 were carried out, and the following steps were carried out.

(c') Deprotection Step

A 4 mol/L hydrochloric acid (0.6 mL) was added to the reaction liquid obtained in the step (b), and the mixture was heated at 125° C. for 5 minutes to obtain an unpurified [$^{18}$F]flutemetamol solution.

(d') First Purification Step

The unpurified [$^{18}$F]flutemetamol solution obtained in the step (c') was cooled, then water (2 mL) was added thereto, and the mixture was passed through a C30 column to hold the [$^{18}$F]flutemetamol. Furthermore, washing was carried out by passing a 40% (v/v) aqueous acetonitrile solution (12 mL) through the C30 column via a reaction vessel, then washing was carried out by passing water (5 mL) through the C30 column. Acetonitrile (2 mL) was passed through this C30 column to collect an eluate.

(e') Second Purification Step

The eluate obtained in the step (d') was purified by passing through a NH$_2$ column, then acetonitrile solution (1 mL) was further passed through the NH$_2$ column, and these solutions were mixed.

(f') Third Purification Step

Water (5 mL) was added to the solution obtained in the step (e'), and passed through an unused C30 column different from the one used in the step (d') to hold the [$^{18}$F]flutemetamol in the C30 column, then washing was carried out by passing water (4 mL) through the C30 column three times. Ethanol (3.5 mL) was passed through the C30 column, and water (9.3 mL) was passed through the C30 column. Each eluate was collected in a vessel to which a 18.8 mmol/L phosphoric acid buffer (37.2 mL) containing 0.7% (w/v) polysorbate 80 and 1.2% (w/v) sodium chloride were added.

The results of Examples 1 to 3 and Comparative Examples 1 and 2 are shown in Table 1. In Table 1, the "radioactivity amount (MBq)" is a radioactivity amount of [$^{18}$F]fluoride ion at the start of synthesis, used in each example and comparative example, the "synthesis time (minute)" is a time required to perform each example and comparative example, and the "radiochemical yield (%)" is a radiochemical yield of [$^{18}$F]flutemetamol based on the radioactivity amount of [$^{18}$F]fluoride ion after attenuation correction at the start of synthesis, the "radiochemical purity (%)" is a radiochemical purity of [$^{18}$F]flutemetamol, and the "total amount of nonradioactive impurities (μg/mL)" is a concentration of nonradioactive impurities in the obtained [$^{18}$F]flutemetamol solution.

The radiochemical purity of [$^{18}$F]flutemetamol and the concentration of nonradioactive impurities were analyzed by the methods shown below.

1. Analysis of Radiochemical Purity of [$^{18}$F]Flutemetamol

The analysis was conducted by TLC. The conditions are as follows.

TLC plate: Silica Gel 60 F$_{254}$ (manufactured by Merck)
Mobile phase: Ethyl acetate/diethylamine=100/1
Measuring device: Rita Star (manufactured by raytest)

2. Analysis of Concentration of Nonradioactive Impurities in the [$^{18}$F]Flutemetamol Solution The analysis was conducted by HPLC equipped with an UV detector. The conditions are as follows.

Column: Luna C18(2) (manufactured by Phenomenex, size: 4.6×150 mm, 3 μm)
Mobile phase: A 20 mmoL ammonium acetate buffer (pH 6.0)/acetonitrile=62/38→40/10 (0→9 minutes), 40/10→10/90 (9→10 minutes), 10/90 (10→20 minutes), 10/90→62/38 (20→20.5 minutes), 62/38 (20.5→30 minutes)
Flow rate: 1.0 mL/minute
Detector: Ultraviolet visible light absorption photometer (detection wavelength: 330 nm)

TABLE 1

| | Radio-activity amount (MBq) | Synthesis time (minute) | Radio-chemical yield (%) | Radio-chemical purity (%) | Total amount of non-radioactive impurities (μg/mL) |
|---|---|---|---|---|---|
| Example 1 | 1570 | 56 | 52.9 | 99.6 | 2.62 |
| Example 2 | 1559 | 54 | 56.0 | 99.6 | 1.98 |
| Example 3 | 1121 | 54 | 55.5 | 99.0 | 1.66 |
| Comparative Example 1 | 1508 | 73 | 41.0 | 94.9 | 1.82 |
| Comparative Example 2 | 1054 | 66 | 30.3 | 92.5 | 0.69 |

As shown in Table 1, the radiochemical yield of [$^{18}$F] flutemetamol was improved by the methods of Examples 1 to 3, and the synthesis time could be shortened. Further, the radiochemical purity was improved, and the marked increase in the total amount of impurities was not found. Therefore, it was shown that, according to the present invention, [$^{18}$F]flutemetamol having the same quality can be obtained while improving the productivity more than a conventional one.

The invention claimed is:

1. A method for producing [$^{18}$F]flutemetamol comprising the steps of:
   (a) reacting a compound of formula (1) with a reactive fluoride

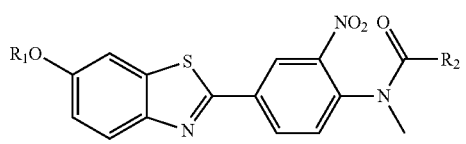

(1)

wherein
—OR$_1$ is selected from hydroxyl or an alkoxymethoxy group having 1 to 6 carbon atoms, and
R$_2$ is selected from hydrogen, alkyls having 1 to 10 carbon atoms, haloalkyls having 1 to 10 carbon atoms, aryls having 6 to 14 carbon atoms, arylalkyls having 6 to 14 carbon atoms, or —(CH$_2$CH$_2$O)$_p$—CH$_3$ wherein p is an integer of 1 to 10;
wherein the reaction of step (a) results in a reaction mixture of the compound of formula (1) and a compound of formula (2):

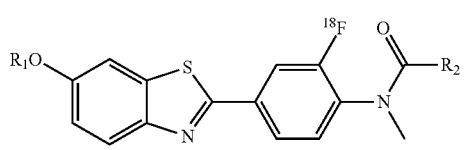

(2)

(b) exposing the reaction mixture of step (a) to a strong base, the reaction mixture of step (a) comprising the compound of formula (1) and the compound of formula (2);
   (c) after the step (b), purifying the compound of formula (2) using a reverse phase solid phase extraction cartridge; and
   (d) removing a protective groups to obtain [$^{18}$F]flutemetamol.

2. The method of claim 1, wherein the step (c) includes the steps of:
   (c-1) holding the compound of formula (2) in a reverse phase solid phase extraction cartridge;
   (c-2) washing the reverse phase solid phase extraction cartridge with a mixture liquid of one or more organic solvents selected from water and a group consisting of acetonitrile, tetrahydrofuran and alkyl alcohols having 1 to 3 carbon atoms; and
   (c-3) eluting the compound of formula (2) with an alkyl alcohol having 1 to 3 carbon atoms from the reverse phase solid phase extraction cartridge.

3. The method of claim 2, wherein, in the step (c-2), the reverse phase solid phase extraction cartridge is washed with a mixture liquid of water and acetonitrile.

4. The method of claim 2, wherein, in the step (c-3), the alkyl alcohol having 1 to 3 carbon atoms is ethanol.

5. The method of claim 1, wherein the reverse phase solid phase extraction cartridge in the step (c) is one packed with triacontyl silylated silica gel.

6. The method of claim 1, further comprising the steps of:
   (e) after the step (d), purifying the [$^{18}$F]flutemetamol using a reverse phase solid phase extraction cartridge; and
   (f) after the step (e), purifying the [$^{18}$F]flutemetamol using a hydrophilic interaction solid phase extraction cartridge.

7. The method of claim 6, wherein the reverse phase solid phase extraction cartridge in the step (e) is one packed with triacontyl silylated silica gel.

8. The method of claim 6, wherein the hydrophilic interaction solid phase extraction cartridge in the step (f) is one packed with aminopropylated silica gel.

9. A method for producing [$^{18}$F]flutemetamol comprising the steps of:
   (a) reacting a compound of formula (1) with a radioactive fluoride to obtain a compound of formula (2),

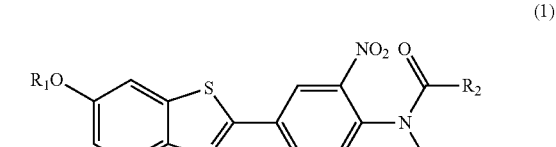

(1)

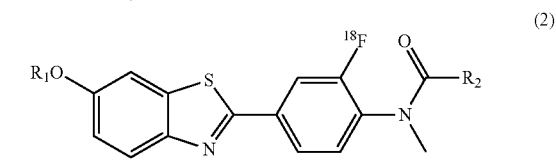

(2)

wherein the group —OR$_1$ is an ethoxymethoxy group or a methoxymethoxy group, and the group R$_2$ is hydrogen or an alkyl having 1 to 10 carbon atoms;
   (b) allowing a strong base to act on the reaction mixture of the step (a) containing the compound of formula (1) and the compound of formula (2) to form a decomposition mixture;
   (c) purifying the decomposition mixture of step (b) to obtain the compound of formula (2) using a reverse phase solid phase extraction cartridge;
   (d) removing a protective group of the compound of formula (2) to obtain [$^{18}$F]flutemetamol;
   (e) purifying the [$^{18}$F]flutemetamol of step (d) using a reverse phase solid phase extraction cartridge to obtain [$^{18}$F]flutemetamol purified after the first purification; and
   (f) further purifying the [$^{18}$F]flutemetamol after the first purification of step (e) using a hydrophilic interaction solid phase extraction cartridge.

10. The method of claim 9, wherein R$_2$ is hydrogen or methyl.

11. The method of claim 9, wherein the step (c) includes the steps of:
   (c-1) holding the compound of formula (2) in a reverse phase solid phase extraction cartridge;

(c-2) washing the reverse phase solid phase extraction cartridge with a mixture liquid of one or more organic solvents selected from water and a group consisting of acetonitrile, tetrahydrofuran and alkyl alcohols having 1 to 3 carbon atoms; and (c-3) eluting the compound of formula (2) with an alkyl alcohol having 1 to 3 carbon atoms from the reverse phase solid phase extraction cartridge.

12. The method of claim 11, wherein, in the step (c-2), the reverse phase solid phase extraction cartridge is washed with a mixture liquid of water and acetonitrile.

13. The method of claim 11, wherein, in the step (c-3), the alkyl alcohol having 1 to 3 carbon atoms is ethanol.

14. The method of claim 10, wherein the reverse phase solid phase extraction cartridge in the step (c) is one packed with triacontyl silylated silica gel.

15. The method of claim 10, wherein the reverse phase solid phase extraction cartridge in the step (e) is one packed with triacontyl silylated silica gel.

16. The method of claim 10, wherein the hydrophilic interaction solid phase extraction cartridge in the step (f) is one packed with aminopropylated silica gel.

17. A method for producing [$^{18}$F]flutemetamol comprising the steps of:
(a) reacting a compound of formula (1) with a radioactive fluoride to obtain a compound of formula (2),

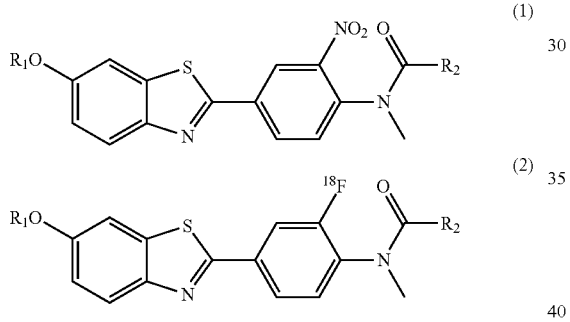

wherein the group —OR$_1$ is an ethoxymethoxy group or a methoxymethoxy group, and the group R$_2$ is hydrogen or methyl;

(b) allowing a strong base to act on the reaction mixture of the step (a) containing the compound of formula (1) and the compound of formula (2) to form a decomposition mixture;

(c) purifying the decomposition mixture of step (b) to obtain the compound of formula (2) using a reverse phase solid phase extraction cartridge packed with triacontyl silylated silica gel;

(d) removing a protective group of the compound of formula (2) to obtain [$^{18}$F]flutemetamol;

(e) purifying the [$^{18}$F]flutemetamol of step (d) using a reverse phase solid phase extraction cartridge packed with triacontyl silylated silica gel to obtain [$^{18}$F]flutemetamol purified after the first purification; and (f) further purifying the [$^{18}$F]flutemetamol after the first purification of step (e) using a hydrophilic interaction solid phase extraction cartridge packed with aminopropylated silica gel.

18. The method of claim 17, wherein the step (c) includes the steps of:
(c-1) holding the compound of formula (2) in a reverse phase solid phase extraction cartridge;
(c-2) washing the reverse phase solid phase extraction cartridge with a mixture liquid of one or more organic solvents selected from water and a group consisting of acetonitrile, tetrahydrofuran and alkyl alcohols having 1 to 3 carbon atoms; and
(c-3) eluting the compound of formula (2) with an alkyl alcohol having 1 to 3 carbon atoms from the reverse phase solid phase extraction cartridge.

19. The method of claim 18, wherein, in the step (c-2), the reverse phase solid phase extraction cartridge is washed with a mixture liquid of water and acetonitrile and in the step (c-3), the alkyl alcohol having 1 to 3 carbon atoms is ethanol.

20. The method of claim 17, wherein the group —OR$_1$ is an ethoxymethoxy group and the group R$_2$ is hydrogen.

* * * * *